US010004918B2

(12) United States Patent
Klang

(10) Patent No.: US 10,004,918 B2
(45) Date of Patent: Jun. 26, 2018

(54) LED BASED VAGINAL LIGHT THERAPY DEVICE

(71) Applicant: Gregg Alan Klang, Trabuco Canyon, CA (US)

(72) Inventor: Gregg Alan Klang, Trabuco Canyon, CA (US)

( * ) Notice: Subject to any disclaimer, the term of this patent is extended or adjusted under 35 U.S.C. 154(b) by 6 days.

(21) Appl. No.: 14/789,992

(22) Filed: Jul. 2, 2015

(65) Prior Publication Data

US 2016/0059034 A1    Mar. 3, 2016

Related U.S. Application Data

(60) Provisional application No. 62/020,874, filed on Jul. 3, 2014.

(51) Int. Cl.
*A61N 5/06* (2006.01)

(52) U.S. Cl.
CPC ......... *A61N 5/0603* (2013.01); *A61N 5/0624* (2013.01); *A61N 2005/0611* (2013.01); *A61N 2005/0626* (2013.01); *A61N 2005/0643* (2013.01); *A61N 2005/0652* (2013.01); *A61N 2005/0663* (2013.01)

(58) Field of Classification Search
CPC . A61B 17/42; A61B 1/303; A61N 2005/0611; A61N 5/0603; A61N 5/0624; A61N 2005/0626; A61N 2005/0643; A61N 2005/0652; A61N 2005/0663
See application file for complete search history.

(56) References Cited

U.S. PATENT DOCUMENTS

| | | | | |
|---|---|---|---|---|
| 2009/0319008 | A1* | 12/2009 | Mayer | 607/90 |
| 2010/0305406 | A1* | 12/2010 | Braun | H01C 7/006 600/202 |
| 2011/0190595 | A1* | 8/2011 | Bennett et al. | 600/301 |
| 2011/0190689 | A1 | 8/2011 | Bennett et al. | |
| 2011/0295186 | A1* | 12/2011 | Klem | 604/20 |
| 2014/0235942 | A1* | 8/2014 | Hellstrom et al. | 600/104 |
| 2016/0008624 | A1* | 1/2016 | Grossman | 607/90 |

OTHER PUBLICATIONS

Korean Intellectual Property Office, Form PCT/ISA/210, International Search Report for corresponding International Application No. PCT/US2016/020532, Jul. 29, 2016, 5 pages.
Korean Intellectual Property Office, Form PCT/ISA/237, Written Opinion for corresponding International Application No. PCT/US2016/020532, Aug. 10, 2016, 10 pages.

* cited by examiner

*Primary Examiner* — Scott T Luan
(74) *Attorney, Agent, or Firm* — William A. English; Vista IP Law Group LLP

(57) ABSTRACT

The embodiments herein provide an LED based vaginal light therapy device for a plurality of bacterial and fungal infections. The device comprises an LED body, a cervix support, a single or a plurality of LEDs, a switch, a tether, microchip and a battery. One end of the device comprises a cervix support to place the device smoothly against the cervix. A plurality of LEDs is provided over the LED body. The LED body comprises one or more LEDs and each LED emits a light having a wavelength in a therapeutic zone of light. The light emitted are in a range of blue light and/or red light. The microchip is housed within the LED body. The microchip connects a battery to the single or plurality of LED's and is further connected to the switch.

25 Claims, 7 Drawing Sheets

LED BASED VAGINAL LIGHT THERAPY DEVICE

CROSS-REFERENCE TO RELATED APPLICATIONS

This application claims the benefit of priority of U.S. Provisional Application No. 62/020,874, filed on Jul. 3, 2014, the disclosure of which is incorporated herein by reference thereto in its entirety.

BACKGROUND

Technical Field of Invention

The embodiments herein generally relate to a medical device and particularly relate to an LED based vaginal light therapy device for treatment of bacterial and fungal infections.

Description of Related Art

Vaginitis is characterized by the inflammation of the vagina that results in discharge, itching and pain. The cause is usually a change in the normal balance of vaginal bacteria or an infection. Vaginitis can also result from reduced estrogen levels after menopause. In a given year as many as 50% of the woman female population experiences bacterial or fungal infection within their vagina. The symptoms range from mucus like discharge, itching, aching, pain during intercourse to odor. The vaginal infections often have multiple causes that present challenging cases for treatment. It is critical to have a balance between naturally occurring yeast and bacteria. It is when the system is out of balance or other types of bacteria are present within the environment does one end up with vaginitis. Indeed, when one cause is treated, the other pathogens become resistant or get mutated when treated with anti-biotic and become resistant to anti-biotic therapies. Sometimes the reduction in good bacteria allows for a propagation of yeast, typically *Candida albicans* resulting in yeast infection. Further, either a change in pH balance or introduction of foreign bacteria in the vagina leads to infectious vaginitis. Physical factors that contribute to the development of an infection include the following: constantly wet vulva due to tight clothing, chemicals coming in contact with the vagina via scented tampons, antibiotics, birth control pills, or a diet favoring refined sugar and yeast.

Bacterial vaginosis also known as vaginal bacteriosis or *Gardnerella* Vaginitis is a disease of the vagina caused by excessive bacteria growth. Common symptoms include increased vaginal discharge that often smells fishlike. The discharge is usually white or gray in color. Burning with urination may also occur. Itching is uncommon. Occasionally there may be no symptoms. Having bacterial vaginosis increases the risk of infection by a number of other sexually transmitted infections including HIV/AIDS. It also increases the risk of early delivery among pregnant women. Bacterial vaginosis is caused by an imbalance of the naturally occurring bacteria in the vagina. Diagnosis is suspected based on the symptom and may be verified by testing the vaginal discharge and finding a higher than normal vaginal pH and large numbers of bacteria. Bacterial vaginosis is often confused with a vaginal yeast infection. Usually treatment is through the use of antibiotics. Bacterial vaginosis is the most common vaginal infection in women of reproductive age. The percentage of women affected at any given time varies between can be as high as 70%. Antibiotics, administered either orally or vaginally are effective in treatment. About 10% to 15% of people, however, do not improve with the first course of antibiotics and recurrence rates of up to 80% have been documented. Recurrence rates are increased with sexual activity with the same pre-post treatment partner and inconsistent condom use although estrogen-containing contraceptives decrease recurrence. There is evidence of an association between Bacterial vaginosis and increased rates of sexually transmitted infections such as HIV/AIDS. Bacterial vaginosis is associated with up to a six-fold increase of HIV shedding. There is also a correlation between the absence of vaginal *lactobacilli* and infection of *Neisseria gonorrhoeae* and *Chlamydia trachomatis*. Bacterial vaginosis is a risk factor for viral shedding and herpes virus type-2 infection. Bacterial vaginosis may increase the risk infection or reactivation of HPV.

Candidiasis, more commonly referred to as a Yeast Infection, is most commonly caused by an overgrowth of a fungus called *Candida albicans* in the vagina. *Candida* is yeast, a type of fungus. Yeast is always present in the vagina in small numbers, and symptoms only appear with overgrowth. *Candida* can multiply when an imbalance occurs, such as when the normal acidity of the vagina changes or when hormonal balance changes. Frequently occurring yeast infections may be a sign of more serious overarching health problem such as diabetes or a compromised immune system. Recurrent infections may also be due to use of antibiotic medications. Recurrent vulvovaginal candidiasis affects at least 75 million women annually in the U.S. About 5-8% of women experience four or more episodes per year, diagnosed as recurrent vulvovaginal candidiasis. About 70% of all pre-menopausal women develop thrush at some point in their lives. With the introduction of over-the-counter medications for home treatment of yeast infections, many women elect to self-diagnose and self-medicate, indicating that the true incidence of yeast infections annually may be significantly under-reported.

In comparison to antibacterial therapy, antifungal treatment is limited to a very small number of drug substances. Treatment for fungal infection can be topical or systemic. Topical antifungals are generally considered as first-line therapy for uncomplicated, superficial, relatively localized fungal infections due to their high efficacy and low potential for systemic adverse effects. Systemic antifungal agents are absorbed and delivered to the body through the blood stream. The oral route is usually the safest, the most economical, and the easiest route for systemic antifungal drugs.

Topical antifungal creams and suppositories have fewer side effects than oral antifungal medications because they aren't absorbed as readily, systemically by the body, and only exert a localized effect on the genital region. Antifungal pills affect the entire body, and side effects can include nausea, headaches, and abdominal pain. However, topical medications can be messy and uncomfortable, while pills are comparatively simple. Treatment using antifungal medication is ineffective in up to 20% of cases. Treatment for thrush is considered to have failed if the symptoms do not clear within 7-14 days. In addition, the incidence of resistance to antifungal agents may be increasing, with drug-resistant fungal strains becoming increasingly common causes of infection in high-risk patient groups such as HIV/AIDS patients. Accordingly, alternative antifungal strategies are being actively sought.

Severe forms of infection are hard to treat, and frequently require more aggressive and long-term therapy, as is the case with chronic, recurrent cases. Additionally, incomplete treatments often result in drug resistant infections therefore full course of therapy should be adhered to.

Alternative Treatment is using a device with a photo-sensitizing agent on yeast infection. In photodynamic antimicrobial chemotherapy (PACT), a combination of a sensitizing drug and visible light causes selective destruction of microbial cells. The ability of light—drug combinations to kill microorganisms has been known for over a century. However, it is only recently with the beginning of the search for alternative treatments for antibiotic-resistant pathogens that the phenomenon has been investigated in detail. Numerous studies have shown PACT to be highly effective in the in vitro destruction of viruses and protozoa, as well as Gram-positive and Gram-negative bacteria and fungi. Light radiation at certain wavelengths causes the death or retarded growth of fungal pathogens residing in human tissue. Reactive Oxygen Species (ROS) can be generated under light-tissue/fungi interaction. Light at certain wavelengths has high efficiency in stimulating generation of ROS in fungal infected areas. Higher power (as compared to traditional low light therapy) of light radiation and prolonged exposure time on tissue creates a fatal concentration of ROS, which is toxic to the pathogen, resulting the retardation or death of the fungi. Under the same circumstances of radiation, the light does not significantly affect healthy human tissue around the infected area. Light radiation only affects local tissue within the radiation zone and has no systemic toxicity.

The market for blue light therapy for micro-organism treatment is somewhat developed, with a number of players offering solutions that appear to offer similar core functionality to the proposed innovation, if somewhat different in form. However, none of the existing products other than the Denta-Ray are designed for use within a body cavity especially the oral cavity, and none of the identified products are designed to target fungal infections, and none are designed for use within the vagina.

While one of the prior arts discloses an intravaginal treatment device (ITD) that provides therapeutic light and fluid treatments. The ITD uses illumination to gather various types of imager data that is used to identify the condition, monitor the treatment process, and evaluate treatment efficacy. Specific frequency light emissions and associated fluids are used to reduce overabundant flora, at least assist in elimination of fungal, viral and bacterial invaders, and enhance the detection process. Several configurations and sizes of ITDs with light and fluid therapy, also have a built in optics assembly (camera, light sources, etc.) for capturing intravaginal still images and video of vaginal channels, cervix, cervical channels, uterus and fallopian tubes. Some ITD configurations are also wearable and include full fluid delivery infrastructure unlike some other ITDs with external components. Supporting devices include local and remotely located computing devices such as laptops, smart phones, and independent monitors. ITDs can be fully or partially inserted via the vaginal channel, and operate in a stand-alone mode or pursuant to remote control. Therapy procedures may be preset or programmed to deliver continuous, periodic and scheduled performance with various underlying parameters defined in the preset or programming processes.

Another prior art discloses a device for treating thevaginal canal by a laser beam, comprising a vaginal canal wall retractor, associated to a system for directing the laser beam towards the wall. This allows using the laser beam for treating the mucosa of the vaginal canal. The main purpose of the treatment that may be performed with the device according to the invention is to prevent and treat atrophic vaginitis, a condition typical but not exclusive of the post-menopause period that currently is normally treated with estrogens for short periods. Atrophic vaginitis is a pathological condition characterized by an inflammation of the vaginal mucosa with progressive decrease of the mucosa thickness due to the loss of collagen structure.

Although, the light therapy treatment of various bacterial, fungal or viral infection in a vaginal canal is known in the prior arts but a treatment of the said infections is majorly achieved through chemical or drug therapies. A use of the said therapies affects an internal functioning of the vagina and uterus as the chemicals used in the form of paste or gel or liquid result in unwanted chemical reactions that are harsh or result in various complications. Also, the light therapy of such infections primarily used within the interior of the vaginal canal has to be achieved through a sophisticated and miniature device being failed to be disclosed or implemented by the known prior arts.

Oral antifungal medications carry the risk of significant side effects, and many patients are allergic to or intolerant of these drugs. Topical solutions can be messy and inconvenient. There are no existing products for the treatment of yeast infections without also requiring medication. Hence there is a need for a product that allows for the treatment of yeast and bacterial infections quickly and simply without systemic effects. With the continued and accelerating emergence of antibiotic-resistant microorganisms, there is burgeoning interest and investment in light therapy. A device that leverages this rising technology could potentially gain rapid acceptance in specific use cases as well as broader support among the general population simply wishing to avoid exposure to additional medications.

In the view of the foregoing, there is a need for a device to treat the intravaginal infections without creating any harmful side effects. Further there is a need for a simple device having a miniature size and the ability to manoeuvre the not-so-easily accessible areas in a vaginal canal.

The above mentioned shortcomings, disadvantages and problems are addressed herein, as detailed below.

SUMMARY OF THE INVENTION

The primary object of the embodiments herein is to provide a miniature intravaginal light therapy device with a progression as well as retreat ability.

Another object of the embodiments herein is to provide an intravaginal light therapy device to treat bacterial and fungal infections without affecting a natural working cycle of uterus or vagina.

Yet another object of the embodiments herein is to provide a simple device for treatment of Vaginitis that works on the principle of killing or rendering inert, the microorganisms especially bacteria and fungi using a light therapy.

Yet another object of the embodiments herein is provide a drug-less therapy for the treatment of vaginal infections.

The embodiments herein provide an LED based vaginal light therapy device for a plurality of bacterial and fungal infections. The device comprises an LED body, a cervix support, a single or a plurality of LEDs, a switch, a tether, microchip and a battery. The LED body is made up of an appropriate medical grade material which allows the therapeutic light to be emitted. The one end of the device comprises a cervix support to place the device smoothly against the cervix. A plurality of LEDs is provided over the LED body. The LED body comprises at-least one LED and each LED emits a light with a wavelength in a therapeutic zone of light in a range of blue and/or red light wavelength. The light emitted is not in the range UV wavelength. The switch is a pressure activated switch. The microchip is housed within the LED body and connects a battery to the single or plurality of LED's and is further connected to the switch. The microchip controls the duration of light therapy and is also used to pulse the light. The pulsing mechanism of light stresses the targeted bacteria or yeast and makes the device more effective. The switch and the LEDs draw power from the battery through the microchip. The switch controls an activation as well as deactivation of the plurality of LEDs. The tether is connected to one end of the LED body and is used for retreating and/or progressing the device.

According to one embodiment herein, the plurality of LEDs emits a non-UV germicidal light with a wavelength ranging between a blue light wavelength and/or a red light wavelength or a Violet light wavelength. The LED emits light in the range of 405 nm-470 nm, according to one embodiment herein. The LEDs emit light in the range of 620 nm-750 nm, according to another embodiment herein. The LEDs emit light in the range of 380 nm-450 nm, according to another embodiment herein. The emitted light kills or limits propagation of various strains of bacteria and fungus.

According to another embodiment herein, the microchip controls the duration of light pulse in a rapid on and/or off manner.

According to one embodiment herein, the hardened material forming the LED body is a medical grade plastic.

According to one embodiment herein, the LED body is sealed to avoid a flow of vaginal fluid into the device.

According to one embodiment herein, the device is non-reusable in nature and serves a treatment of bacterial and fungal infection for single time.

According to one embodiment herein, the device is reusable in nature and serves a treatment of bacterial and fungal infection for multiple times. The reusable device has a washable or rinse-able LED body. The re-usable device incorporates a mini-USB cable appropriate for use as a tether and for recharging the device.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

DETAILED DESCRIPTION OF THE DRAWINGS

Figure 1A:
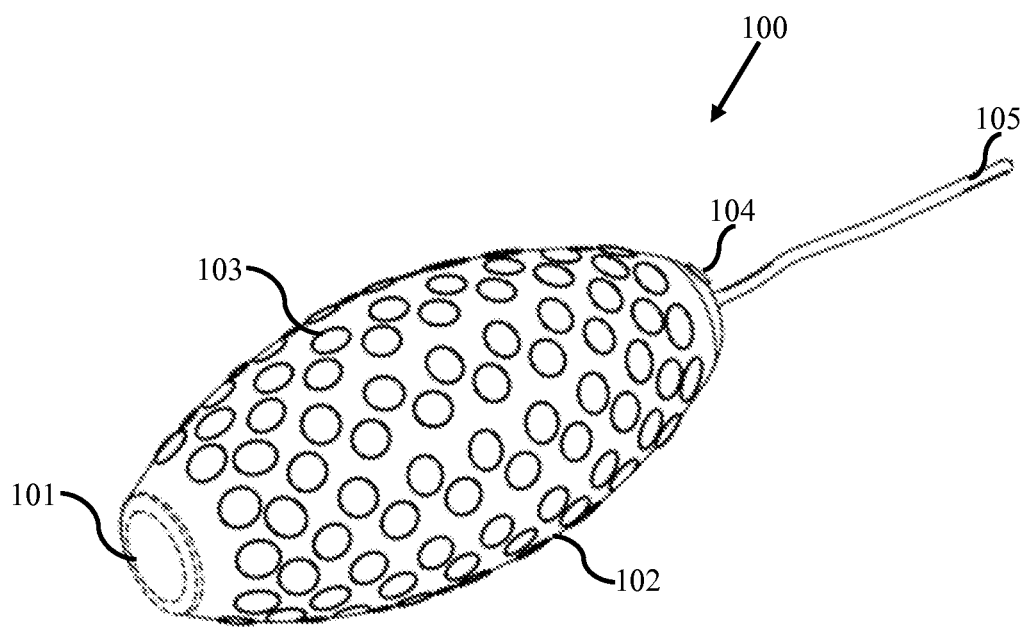
FIG. 1A illustrates a perspective view of the LED based vaginal light therapy device, according to one embodiment herein.

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein provide an LED based vaginal light therapy device for a plurality of bacterial and fungal infections. The device comprises an LED body, a cervix support, a single or a plurality of LEDs, a switch, a tether, microchip and a battery. The LED body is made up of an appropriate medical grade material which allows the therapeutic light to be emitted. One end of the device comprises a cervix support to place the device smoothly against the cervix. A single or multiple LEDs are provided over the LED body. Each LED emits a light with a wavelength in a therapeutic zone of light in a range of blue and/or red light or Violet light (germicidal non UV) wavelength. The light emitted is not in the range UV wavelength. The switch is a pressure activated switch. The microchip is housed within the LED body and connects a battery to the single or plurality of LED's and is further connected to the switch. The microchip controls the duration of light therapy and is also used to pulse the light. The pulsing mechanism of light stresses the targeted bacteria or yeast and makes the device more effective. The switch and the LEDs draw a power from the battery through the microchip. The switch controls an activation as well as deactivation of the plurality of LEDs. The tether is connected to one end of the LED body and is used for retreating and/or progressing the device.

According to one embodiment herein, the plurality of LEDs emits a non-UV germicidal light with a wavelength ranging between a blue light wavelength and/or a red light wavelength or a Violet light wavelength. The LED emits light in the range of 405 nm-470 nm, according to one embodiment herein. The LEDs emit light in the range of 620 nm-750 nm, according to another embodiment herein. The LEDs emit light in the range of 380 nm-450 nm, according to another embodiment herein. The emitted light kills or limits propagation of various strains of bacteria and fungus.

According to one embodiment herein, the microchip controls the duration of light pulse in a rapid on and/or off manner.

According to one embodiment herein, the hardened material forming the LED body is a medical grade plastic.

According to one embodiment herein, the LED body is sealed to avoid a flow of vaginal fluid into the device.

According to one embodiment herein, the device is non-reusable in nature and serves a treatment of bacterial and fungal infection for single use. Further, the device is reusable in nature and serves a treatment of bacterial and fungal infection for multiple times by using a mini-USB cable as a tether and for recharging the device, according to another embodiment herein. The reusable device has a washable or rinse-able LED body 102 having an ellipsoid shape, as shown in FIGS. 1A-1F.

Figure 1B:
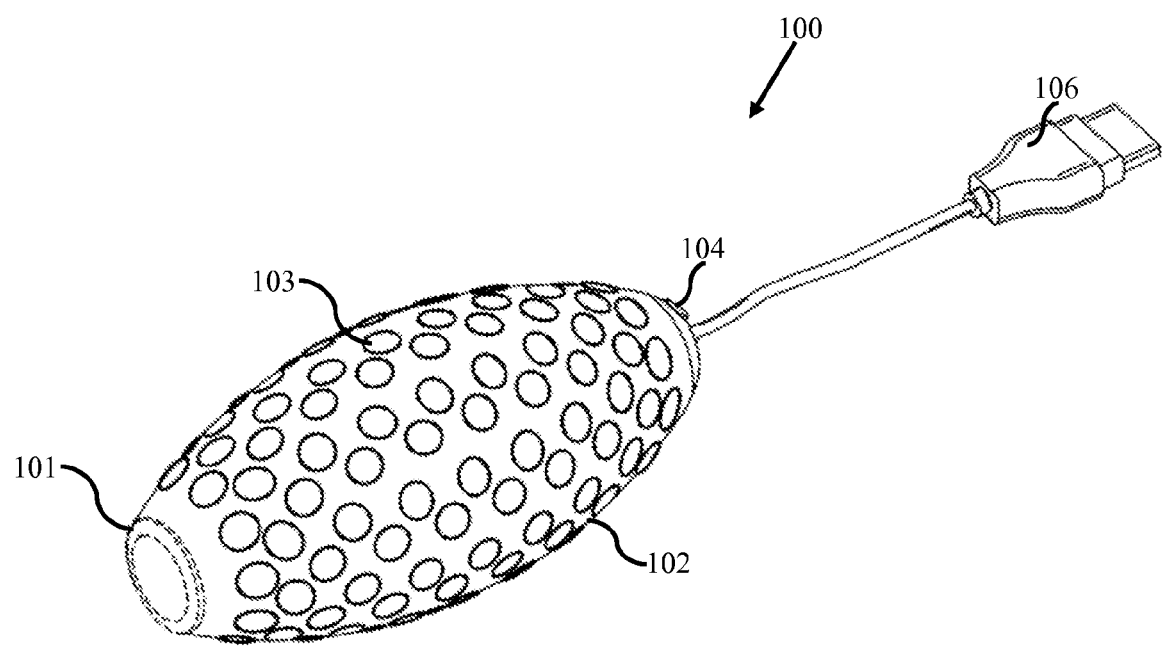
FIG. 1B illustrates a perspective view of the LED based vaginal light therapy device with a USB cord, according to one embodiment herein.
Figure 1C:
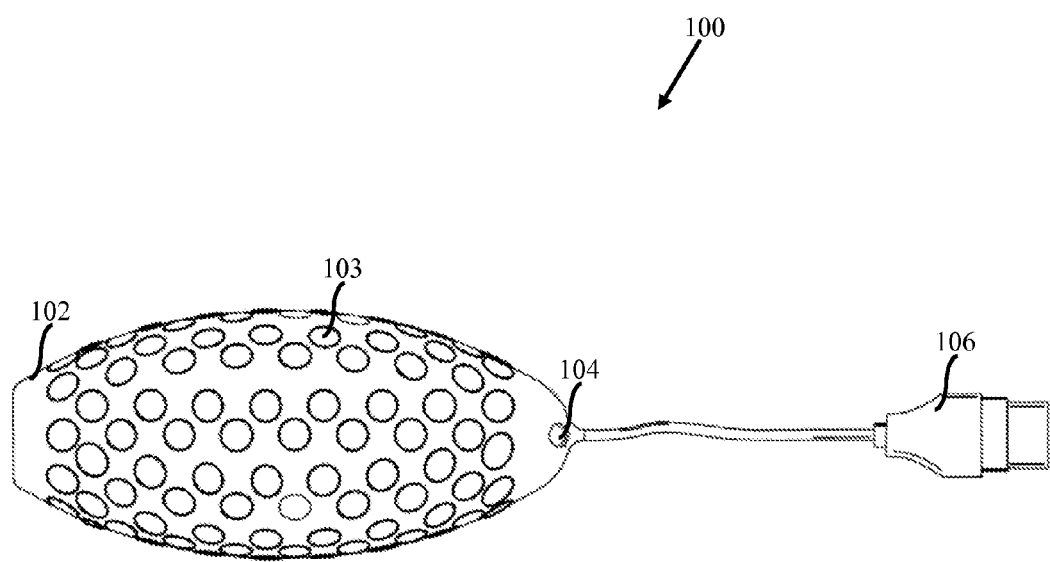
FIG. 1C illustrates a top view of the LED based vaginal light therapy device, according to one embodiment herein.
Figure 1D:
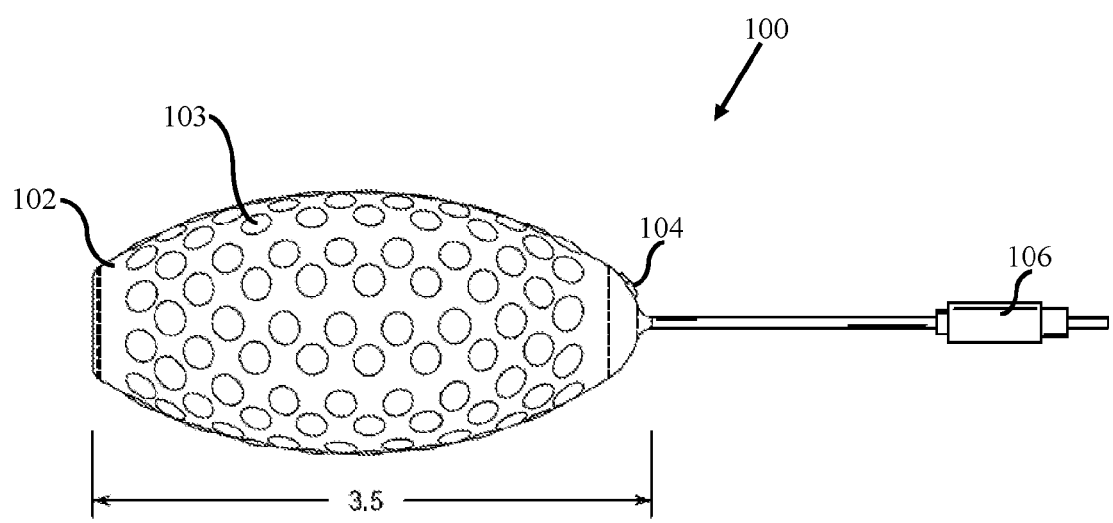
FIG. 1D illustrates a side view of the LED based vaginal light therapy device, according to one embodiment herein.
Figure 1E:
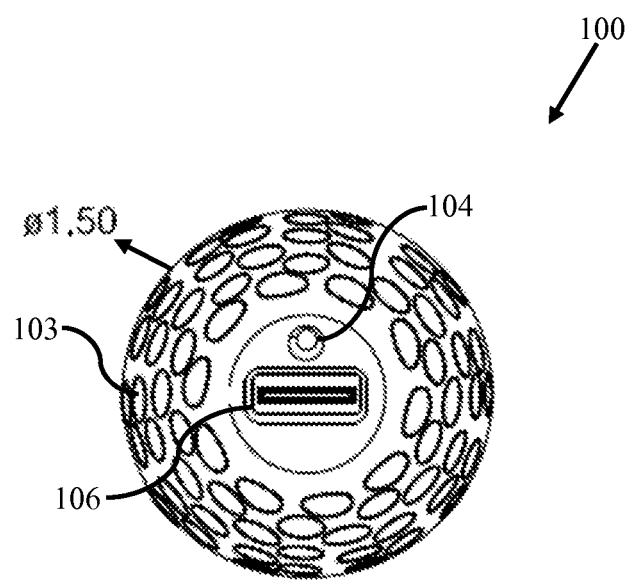
FIG. 1E illustrates a front view of the LED based vaginal light therapy device, according to one embodiment herein.
Figure 1F:
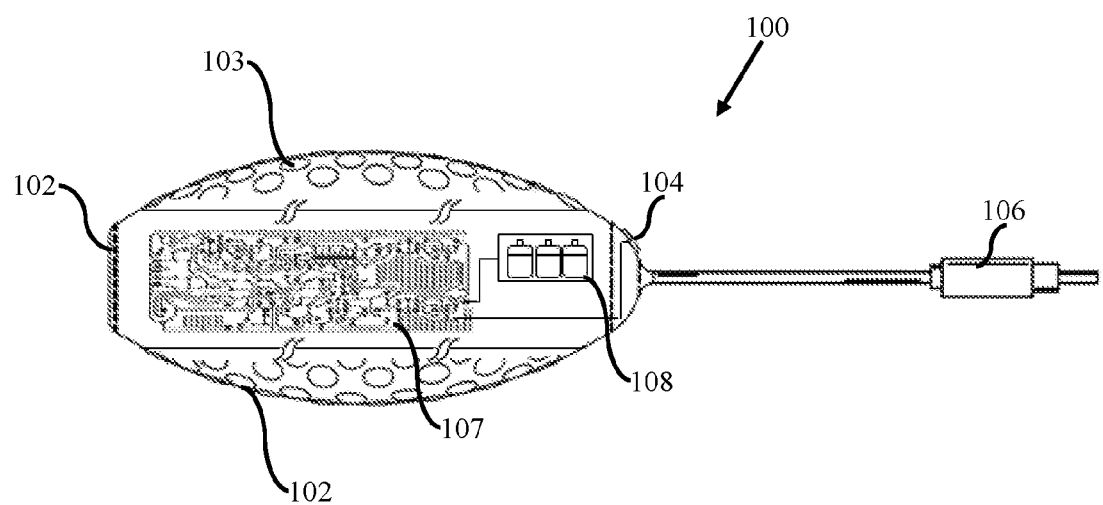
FIG. 1F illustrates a sectional view of the LED based vaginal light therapy device, according to one embodiment herein.

FIG. 1A illustrates a perspective view of the LED based vaginal light therapy device, according to one embodiment herein. FIG. 1B illustrates a perspective view of the LED based vaginal light therapy device with a USB cord, according to one embodiment herein. FIG. 1C-1F illustrates a top view, a side view, a front view and a sectional view respectively of the LED based vaginal light therapy device, according to one embodiment herein. With respect to FIGS. 1A-1F, the LED body 102 of the light therapy device 100 is primarily a plastic framework which allows positioning of single or multiple LEDs 103 on an external surface. The battery 108, the microchip 107 and additional electronic controllers and circuits are positioned internally with respect to the LED 103. The pressure activated switch 104 is located on the outer surface. The device 100, once assembled, is encased into an appropriate medical grade plastic housing which is completely sealed until not serviceable. A suitable tether 105 or a mini-USB cable 106 is attached at the second end to assist in progression or retreat of the device inwards or outwards of the vaginal canal. The one end of the device comprises a cervix support 101 to place the device smoothly against the cervix.

The length of the LED body is but not limited to 3.5 inches and has a diameter of 1.5 inches. The surface of LED body is either rigid or squeezable depending on the basis of user preference and area of usage. The device is used for hand sanitization also.

Figure 2:
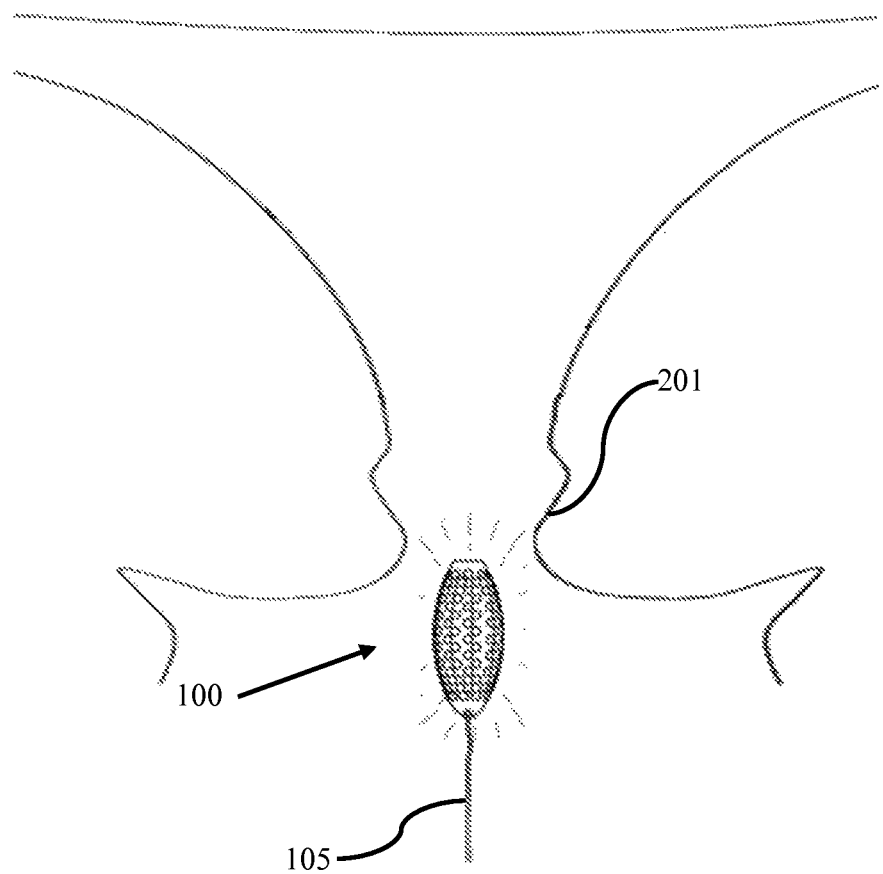
FIG. 2 illustrates a placement of the vaginal light therapy device inside a vaginal canal of a female, according to one embodiment herein.

FIG. 2 illustrates a placement of the vaginal light therapy device inside the vaginal canal of a female, according to one embodiment herein. With respect to FIG. 2, the device 100 is inserted into the vaginal canal 201 through the USB cable 106. The device 100 is activated through the pressure activated switch before inserting the device 100 into the vagina after it reaches a predetermined position in the vaginal canal 201 and starts emitting the light. The device 100 is left in the vagina for a specific period of time varying from few minutes to hours depending upon extent of infection and kind of infection (bacterial or fungal).

The light therapy device disclosed herein provides a harmless and efficient treatment of the intravaginal infection. Since the device does not reacts with any vaginal fluid, thus can be used in any patient's condition. Also the device has low cost and easy usage procedure, so it is usable even personally after a physician's approval.

According to an embodiment herein, the device is effective for the treatment of fungal and bacterial vaginitis. In case of bacterial vaginitis, there is no need for the use of additional photo sensitizing agents as bacteria are negatively affected by the light based therapy of the present invention.

The present invention helps to eliminate or reduce undesirable microorganisms as an adjunct and forms a basis for the replacement of traditional therapies. The present invention is useful for the patients who are interested in non-drug therapies. The patients who cannot tolerate oral or topical azole therapy, as well as immune-compromised patients with recurrent yeast or bacterial infections can be treated with the present invention.

According to one embodiment herein, the device is effective against fungal as well as bacterial infections. The fungal infection comprises the infection caused by yeast and especially by *Candida albicans* while the bacterial infection comprises the infection caused principally by *Gardnerella*. The patient has to determine first whether he is suffering from a fungal infection or a bacterial infection. This can be determined first through a doctor's test.

According to an embodiment herein, the device is sold along a testing strip. The testing strip is used for the determination of the fungal and the bacterial infection suffered by a patient according to the embodiments herein. The bacterial as well as fungal infections are treated using the device of the present invention as an alternative to drugs, douches or chemicals prescribed by a doctor.

According to another embodiment herein, in case of fungal infection, the device is used along with a photo-sensitizer. The photo-sensitizer is needed in cases of yeast infection. The photo sensitizer comprises porfimer sodium (Photofrin), 5-aminolevulinic acid or ALA (Levulan), and methyl aminolevulinate [MAOP] (Metvix).

According to one embodiment herein, the device is a low power long duration therapy so as to be safer for the mucosal tissue. The idea is that the device can be inserted overnight and pulled in the morning. The LEDs are single color or multi color LEDs, pulsed or non pulsed lights.

According to one embodiment herein, the device is made as a single use device.

According to another embodiment herein, the device is made for multiple usages. For multiple usages the device is paired with a rechargeable battery and a cord which facilitates the removal of the device from the vagina as well as acts as a connection with a suitable power source in order to recharge the device.

According to one embodiment herein, the light therapy device comprises one or more LEDs as light source for impending light on the vaginal walls. The device further comprises battery housed inside the 100% sealed housing or the LED body. The battery acts as power source and connected to the microchip as well as the LEDs. The microchip controls a duration of the light therapy. A printed circuit or a suitable electronic circuitry or hub is provided in the device for interconnecting the switch, the LEDs, the microchip and the battery. The device further comprises switch activates a device to start the light therapy. The device also comprises a tether for retrieval of the device during a light therapy. The tether is suitably replaced by a USB cord or a charging cord for making device suitable for multiple usage.

According to the embodiments herein, the device either kills or renders inert the targeted species which keeps species from replicating. The device is also used as an adjunct therapy with existing known treatments possibly allowing for a reduction in drug or chemical based therapies. If the device is used with the conventional therapies then the device is likely to reduce the treatment times.

The purpose of this invention is to provide a non drug based alternative therapy based on safe and germicidal light which when introduced into the region provides a safe and effective method to treat and control both Yeast and Bacterial infection. The device effectiveness may be enhanced through the use of a photo-sensitizer. The device may be used in conjunction with standard systemic drug or topical cream based therapies to lessen the duration of the event.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

I claim:

1. An LED based vaginal light therapy device for treating a variety of bacterial and fungal infections, comprising:
   an LED body having an ellipsoid shape including a rounded proximal end, a distal end, a relatively large diameter central region substantially midway between the proximal end and the distal end, a proximal tapered region tapering from the central region to the proximal end, and a distal tapered region tapering from the central region to a cervix support surface at the distal end shaped to place the device smoothly against a vaginal cervix, the LED body sized for introduction entirely into a vagina such that the distal end is disposed adjacent the cervix and the proximal end is disposed within the vagina beyond an entrance to the vagina, wherein the LED body is made up of a hardened material;

one or more LEDs carried by the LED body, wherein each LED emits a light having a wavelength in a range of non-UV germicidal light;

a switch, wherein the switch is a pressure activated switch present on the LED body;

a microchip and a battery housed within the LED body, wherein the microchip connects the battery to the one or more LEDs, wherein the microchip is further connected to the switch for activating the one or more LEDs;

a tether extending from the proximal end of the LED body for retreating and/or progressing the device through a vagina of a patient;

wherein, the switch and the one or more LEDs draw a power from the battery through the microchip, wherein the switch controls an activation as well as deactivation of the one or more LEDs on the basis of a pressure sensing by the intravaginal walls.

2. The device according to claim 1, wherein the non-UV germicidal light comprises a range of blue light with 405 nm-470 nm wavelength.

3. The device according to claim 1, wherein the non-UV germicidal light comprises a range of red light with 620 nm-750 nm wavelength.

4. The device according to claim 1, wherein the non-UV germicidal light comprises a range of Violet light with 380-450 nm wavelength.

5. The device according to claim 1, wherein the microchip controls a duration of light pulses emitted by the one or more LEDs in a rapid on and/or off manner.

6. A device for vaginal light therapy of a patient, comprising:

a body including a rounded proximal end, a distal end, the body having a substantially prolate spheroid shape and sized for introduction entirely into a vagina such that the distal end is disposed adjacent a vaginal cervix and the proximal end is disposed within the vagina beyond an entrance to the vagina, the body including a relatively large diameter central region substantially midway between the proximal end and the distal end, a proximal tapered region tapering from the central region to the proximal end and distal tapered region tapering from the central region to a cervix support surface at the distal end shaped to place the device smoothly against the cervix;

one or more light sources carried on the body, each light source configured to emit light outwardly from the body at one or more wavelengths to treat fungal or bacterial vaginitis;

a controller within the body coupled to the one or more light sources for controlling operation of the one or more light sources; and a tether extending from the proximal end of the body and configured for retrieving the device from a vagina of a patient.

7. The device of claim 6, wherein the body defines an outer surface extending between the proximal and distal ends, and wherein the one or more light sources comprise a plurality of light sources on the outer surface.

8. The device of claim 6, wherein the controller is configured to activate the one or more light sources to pulse.

9. The device of claim 6, further comprising a switch on the body coupled to the one or more light sources for selectively activating the one or more light sources.

10. The device of claim 9, wherein the switch is configured to control activation of the one or more light sources based at least in part on pressure sensing intravaginal walls of a vagina within which the device is introduced.

11. The device of claim 6, wherein the tether is a cord including a connector for coupling the device to an external power source.

12. The device of claim 6, wherein the one or more light sources emit light at one or more wavelengths between 380 nm and 750 nm.

13. The device of claim 6, wherein the one or more light sources emit light at one or more wavelengths of visible blue light.

14. The device of claim 6, further comprising a photosensitizer.

15. The device of claim 6, wherein the cervix support surface is a substantially flat surface.

16. The device of claim 6, further comprising a battery within the body for powering the controller and the one or more light sources, and wherein the tether comprises a cord for coupling the device to an external power source for charging the battery.

17. A method for vaginal light therapy of a patient, comprising:

providing a body having an ellipsoid shape defining a relatively large diameter central region substantially midway between a proximal end and a distal end of the body, a proximal tapered region tapering from the central region to the proximal end, and a tapered distal region tapering from the central region to a cervix support surface at the distal end shaped to place the device smoothly against the cervix;

inserting the body entirely into a vagina such that the distal end is disposed adjacent a vaginal cervix and the proximal end is disposed within the vagina beyond an entrance to the vagina and a tether extending from the proximal end of the body exits the vagina; and activating one or more light sources carried on the body, each light source emitting light outwardly from the body at one or more wavelengths to treat fungal or bacterial vaginitis; and removing the body from the vagina using the tether.

18. The method of claim 17, wherein the body defines an outer surface extending between proximal and distal ends, and wherein the one or more light sources comprise a plurality of light sources on the outer surface with no light sources on the cervix support surface.

19. The method of claim 17, wherein the one or more light sources emit light at one or more wavelengths within a range of non-UV germicidal light.

20. The method of claim 17, wherein the one or more light sources emit light at one or more wavelengths between 380 nm and 750 nm.

21. The method of claim 17, wherein the one or more light sources emit light at one or more wavelengths of visible blue light.

22. The method of claim 17, wherein the body is inserted into the vagina and left overnight and is removed from the vagina the following morning.

23. The method of claim 17, wherein the tether is a cord.

24. The method of claim 17, wherein the one or more light sources are activated by a switch on the body.

25. The method of claim 17, wherein the one or more light sources are activated using a pressure activated switch after the body reaches a predetermined position in the vagina and starts emitting the light.

\* \* \* \* \*